(12) United States Patent
Kim et al.

(10) Patent No.: US 11,970,686 B2
(45) Date of Patent: Apr. 30, 2024

(54) BEVERAGE MAKER AND METHOD FOR CONTROLLING BEVERAGE MAKER

(71) Applicant: LG ELECTRONICS INC., Seoul (KR)

(72) Inventors: Youngjoon Kim, Seoul (KR); Daewoong Lee, Seoul (KR); Jinpyo Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 1066 days.

(21) Appl. No.: 16/701,481

(22) Filed: Dec. 3, 2019

(65) Prior Publication Data

US 2020/0181559 A1 Jun. 11, 2020

(30) Foreign Application Priority Data

Dec. 5, 2018 (KR) .......................... 10-2018-0155118

(51) Int. Cl.
*C12M 1/34* (2006.01)
*C12C 11/00* (2006.01)
*C12C 13/10* (2006.01)

(52) U.S. Cl.
CPC ........... *C12M 41/12* (2013.01); *C12C 11/006* (2013.01); *C12C 13/10* (2013.01)

(58) Field of Classification Search
CPC ....... C12C 13/10; C12C 11/006; C12M 41/12
See application file for complete search history.

(56) References Cited

U.S. PATENT DOCUMENTS

2017/0029752 A1* 2/2017 Mitchell ................. C12C 13/10

\* cited by examiner

*Primary Examiner* — Shogo Sasaki
(74) *Attorney, Agent, or Firm* — KED & ASSOCIATES

(57) ABSTRACT

A beverage maker may include a fermentation tank including a space in which a beverage is made, a refrigerant cycle device to cool the fermentation tank, a temperature sensor to detect a temperature of the fermentation tank, and a controller to drive the refrigerant cycle device to decrease a temperature of the fermentation tank which accommodates a mixture including an ingredient of the beverage to a fermentation temperature while the beverage is being made, to stop driving of the refrigerant cycle device when the temperature detected by the temperature sensor reaches a first step temperature of a plurality of step temperatures set higher than the fermentation temperature, and to re-drive the refrigerant cycle device after a predetermined period of time has elapsed.

11 Claims, 5 Drawing Sheets

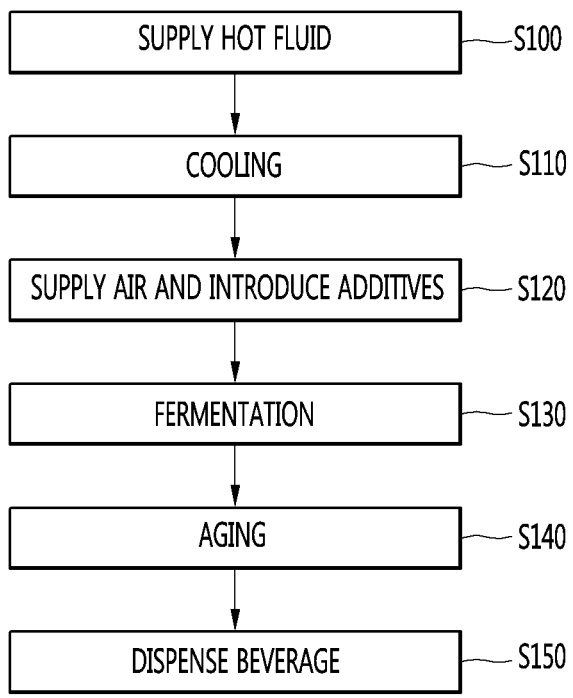
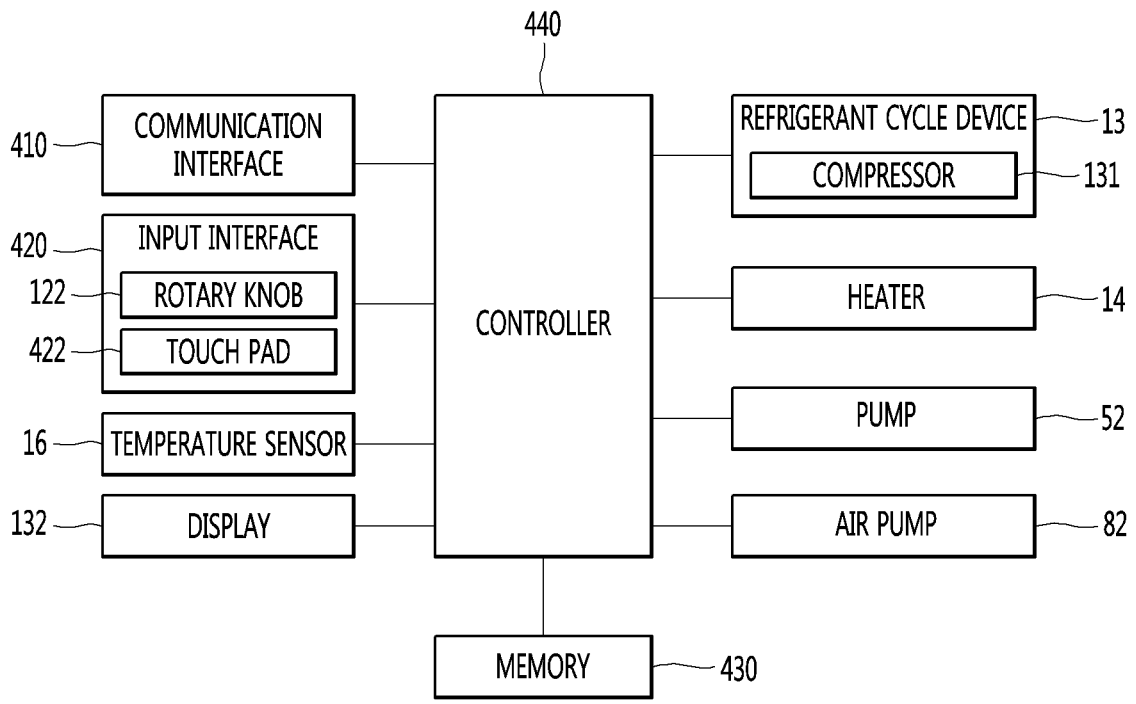

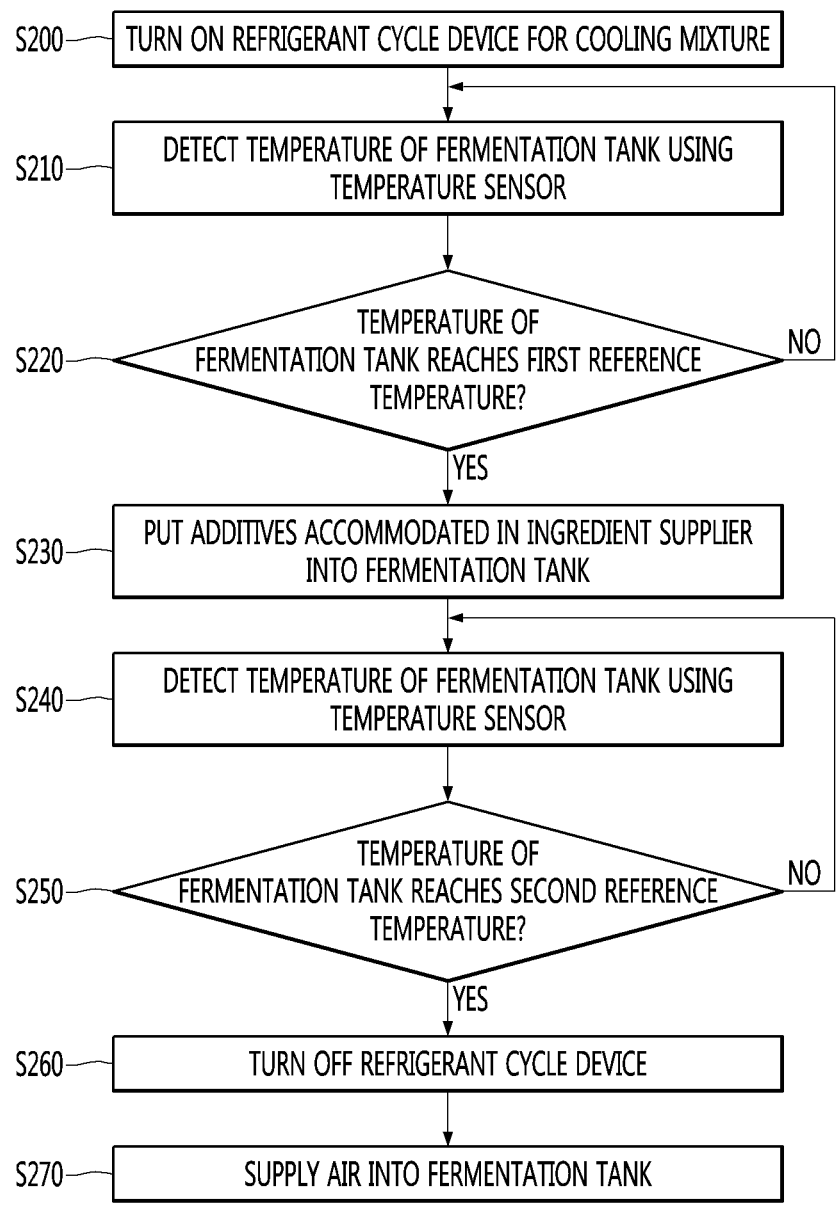

BEVERAGE MAKER AND METHOD FOR CONTROLLING BEVERAGE MAKER

CROSS-REFERENCE TO RELATED APPLICATION(S)

This application claims priority under 35 U.S.C. 119 and 365 to Korean Patent Application No. 10-2018-0155118, filed in Korea on Dec. 5, 2018 in the Korean Intellectual Property Office, the disclosure of which is incorporated herein by reference.

BACKGROUND

1. Field

A beverage maker and a method for controlling a beverage maker are disclosed herein.

2. Background

Beverages are collectively referred to as drinkable liquids, such as alcohol or tea. For example, beverages may be divided into various categories, such as water (a beverage) for quenching thirst, juice beverages with a unique flavor and taste, refreshing beverages giving a refreshing sensation, favorite beverages with a stimulant effect, or alcoholic beverages with an alcohol effect.

A representative example of such a beverage is beer. Beer is an alcoholic beverage produced by making juice of malt, which is made by sprouting barley, filtering the juice, adding hop, and fermenting yeast.

Consumers may purchase ready-made products made and sold by a beer maker or may make beer at home (hereinafter "homemade" beer) produced by directly fermenting beer ingredients at home or in a bar. Homemade beer may be made in a variety of types rather than ready-made products and may be made to better suit a consumer's taste.

The ingredients for making beer may include water, liquid malt, hop, yeast, and a flavoring additive, for example. Leaven, which is called yeast, may be added to liquid malt to ferment the liquid malt and assist production of alcohol and carbonic acid. Flavor additives are additives that enhance the taste of beer, such as fruit, syrup, and vanilla beans, for example.

Generally, homemade beer may include three stages or operations, namely, a wort stage or operation, a fermentation stage or operation, and an aging stage of operation, and it may take about two to three weeks from the wort stage or operation to the aging stage or operation. Maintaining an optimum temperature during the fermentation operation is important for homemade beer, and the easier the beer is to make, the more user convenience is improved. Recently, a beverage maker capable of easily making a beer-like beverage at home or in a bar has been gradually used, and such a beverage maker is configured to be convenient.

BRIEF DESCRIPTION OF THE DRAWINGS

Embodiments will be described in detail with reference to the following drawings in which like reference numerals refer to like elements, and wherein:

FIG. 2 is a flowchart of an operation for making a beverage in a beverage maker according to an embodiment;

FIG. 3 is a schematic block diagram showing control components of a beverage maker according to an embodiment;

FIG. 4 is a flowchart of a cooling operation, an air supply operation, and an additives introduction operation during the beverage making operation described above with reference to FIG. 2;

DETAILED DESCRIPTION

Figure 1:
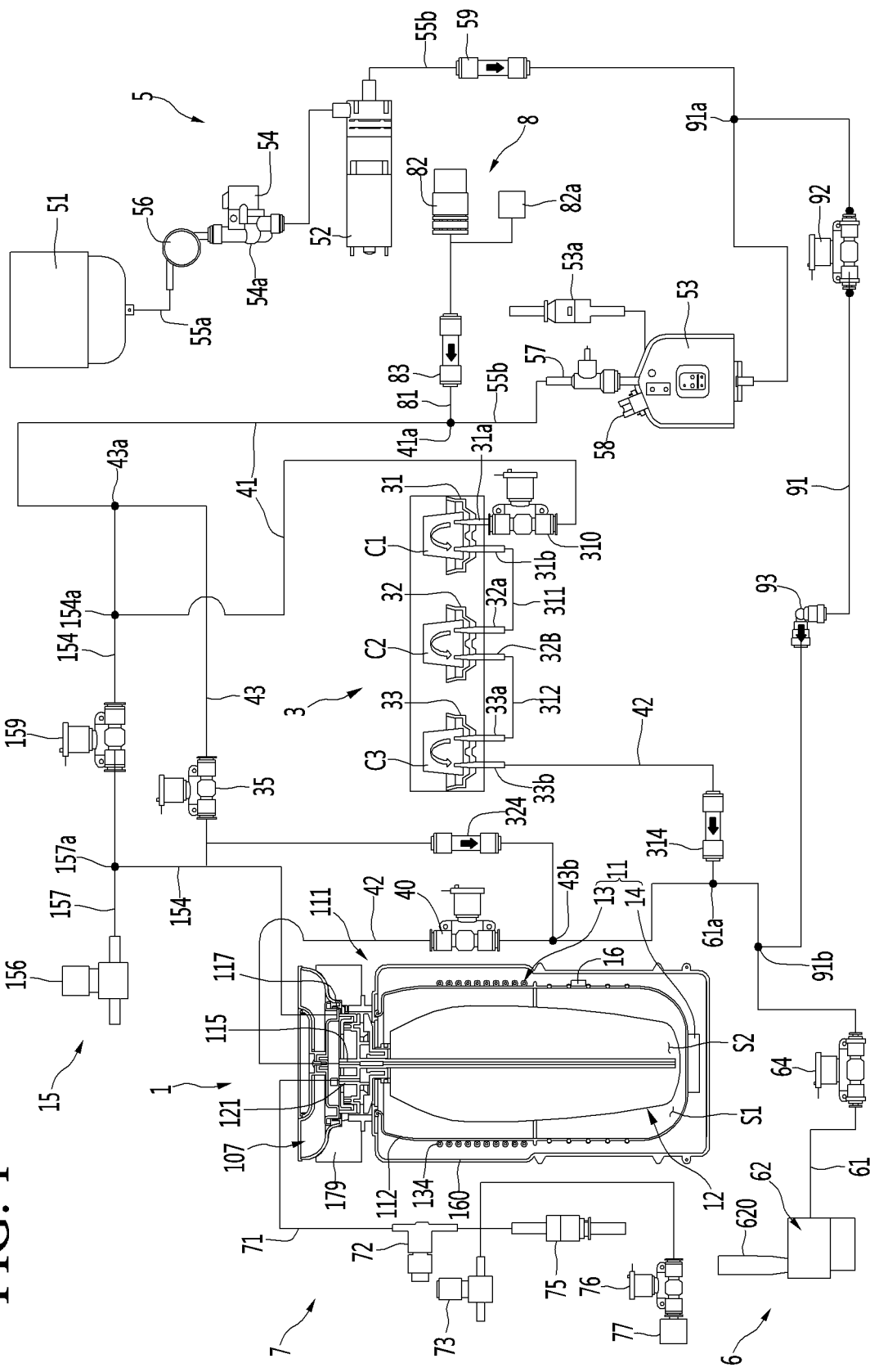
FIG. 1 is a schematic view of a beverage maker according to an embodiment.

Hereinafter, embodiments are described with reference to drawings. Wherever possible, like or the same reference numerals have been used to indicate like or the same elements, and repetitive disclosure has been omitted.

Although beer is exemplified as a beverage that is made using a beverage maker according to embodiments, the kind of beverage that can be made using the beverage maker is not limited to beer and various kinds of beverages may be made using the beverage maker according to embodiments.

FIG. 1 is a schematic view of a beverage maker according to an embodiment. The beverage maker may include a fermentation module 1. A beverage may be fermented in the fermentation module 1. The beverage maker may include a temperature controller that controls an inner temperature of the fermentation module 1.

The beverage maker may include a fluid supply module 5. The fluid supply module 5 may supply a fluid, such as water.

The beverage maker may include an ingredient supplier 3 provided with ingredient receivers 31, 32, and 33 in which ingredients required for making a beverage may be accommodated. The beverage maker may include main channels 41 and 42 that connect the fluid supply module 5 to the fermentation module 1.

The beverage maker may include a beverage dispenser 6 that dispenses the beverage made in the fermentation module 1 to the outside. The beverage dispenser 6 may be connected to second main channel 42. Thus, the beverage dispensed from the fermentation module 1 may be guided to the beverage dispenser 6 by passing through a portion of the second main channel 42.

The beverage maker may further include a gas discharger 7. The gas discharger 7 may be connected to the fermentation module 1 to discharge a gas generated while the beverage is made.

The beverage maker may further include an air injector 8 that injects air. The air injector 8 may be connected to the fluid supply module 5 or first main channel 41. The air injector 8 may include an air pump 82.

The beverage maker may further include an air controller 15 that controls a pressure between an inner wall of a fermentation tank 112 and an outer surface of a fermentation container 12. The beverage maker may further include a sub channel 91. The sub channel 91 may connect the fluid supply module 5 to the beverage dispenser 6.

The fermentation module 1 may include a fermentation tank module 111 having an opening, and a fermentation lid 107 that opens and closes the opening. The fermentation tank module 111 may include a fermentation case 160 and fermentation tank 112 accommodated in the fermentation case 160 and having an inner space S1. Insulation (not shown) may be provided between the fermentation case 160 and the fermentation tank 112. The fermentation tank module 111 may further include a lid seating body 179 on which the fermentation lid 107 may be seated.

Each of the fermentation case 160 and the fermentation tank 112 may be provided as an assembly of a plurality of members or components. The fermentation case 160 may define an outer appearance of the fermentation tank module 111.

The fermentation lid 107 may seal an inside of the fermentation tank module 111 and be disposed on the fermentation tank module 111 to cover the opening. A main channel, more particularly, a main channel connecting portion 115 connected to the second main channel 42 may be provided in the fermentation lid 107.

A fermentation container 12 may be accommodated in the fermentation tank 112. The fermentation container 12 may be provided as a separate container so that beverage ingredients and a finished beverage do not stain the inner wall of the fermentation tank 112. The fermentation container 12 may be separably disposed on or in the fermentation tank 112. The fermentation container 12 may be seated on or in the fermentation tank 112 to ferment the beverage within the fermentation tank 112. After the fermentation container 12 is used, the fermentation container 12 may be removed from the fermentation tank 112.

The fermentation container 12 may be a pack containing ingredients for making a beverage. The fermentation container 12 may be made of a flexible material. Thus, the fermentation container 12 may be easily inserted into the fermentation tank 112 and be contracted and expanded by a pressure. However, embodiments are not limited thereto. For example, the fermentation container 12 may be made of a PET material.

The fermentation container 12 may have a beverage-making space S2 in which beverage ingredients may be accommodated, and the beverage made. The fermentation container 12 may have a size less than a size of inner space S1 of the fermentation tank 112.

The fermentation container 12 may be inserted into and accommodated in the fermentation tank 112 in a state in which the ingredients are contained in the fermentation container 12. The fermentation container 12 may be inserted into the fermentation tank 112 and then accommodated in the fermentation tank 112 in a state in which the fermentation lid 107 is opened.

The fermentation lid 107 may seal the fermentation tank 112 after the fermentation container 12 is inserted into the fermentation tank 112. The fermentation container 12 may assist fermentation of the ingredients in a state in which the fermentation container 12 is accommodated in the inner space S1 sealed by the fermentation container 112 and the fermentation lid 107. The fermentation container 12 may be expanded by pressure therein during the making of the beverage. The fermentation container 12 may be pressed by air within the fermentation tank 112 when the beverage contained in the fermentation container 12 is dispensed, and the air may be supplied between the inner surface of the fermentation tank 112 and the fermentation container 12.

As the fermentation container 12 is accommodated in the fermentation tank 112 and the fermentation lid 107 is closed, the main channel connecting portion 115 of the fermentation lid 107 may connect the second main channel 42 and the beverage-making space S2 inside of the fermentation container 12. Thus, fluid, such as water supplied from the fluid supply module 5 while the beverage is made may be injected into the fermentation container 12 through the second main channel 42 and the main channel connecting portion 115. An ingredient accommodated in the ingredient supplier 3 may be injected into the fermentation container 12 through the second main channel 42 and the main channel connecting portion 115. A finished beverage contained in the fermentation container 12 may pass through the main channel connecting portion 115, the second main channel 42, and a beverage dispensing channel 61 and may be dispensed to the outside through a dispenser 62.

The beverage maker according to embodiments may inject the fluid and ingredients supplied while the beverage is made into the fermentation container 12 through the main channel connecting portion 115 formed on the fermentation lid 107. The beverage maker may dispense the beverage accommodated in the fermentation container 12 by the dispenser 62 through the main channel connecting portion 115. That is, the beverage maker according to embodiments may inject or dispense a fluid, such as water, ingredients, and a beverage through the main channel connecting portion 115 formed on the fermentation lid 107, thereby simplifying a configuration for connection between the second main channel 42 and the fermentation container 12.

The fermentation tank 112 may be disposed in the fermentation case 160. The fermentation tank 112 may have an outer circumferential surface and an outer bottom surface, which may be spaced apart from an inner surface of the fermentation case 160. The outer circumferential surface of the fermentation tank 112 may be spaced apart from an inner circumference of the fermentation case 160, and the outer bottom surface of the fermentation tank 112 may be spaced apart from an inner bottom surface of the fermentation case 160.

The insulation (not shown) may be provided between the fermentation case 160 and the fermentation tank 112. The insulation may be disposed in the fermentation case 160 to surround the fermentation tank 112. Thus, a temperature of the fermentation tank 112 may be maintained constant. The insulation may be made of a material, such as foamed polystyrene or polyurethane, which has a high thermal insulating performance and absorbs vibration.

The fermentation tank 112 may include a temperature sensor 16 that measures a temperature of the fermentation tank 112. The temperature sensor 16 may be mounted on the outer circumferential surface of the fermentation tank 112. The temperature sensor 16 may be disposed below an evaporator 134 wound around the fermentation tank 112.

A temperature controller 11 may change an inner temperature of the fermentation tank module 111. The temperature controller 11 may change a temperature of the fermentation tank 112. The temperature controller 11 may heat or cool the fermentation tank 112 to control a temperature of the fermentation tank 112 at an optimal temperature for fermenting the beverage.

The temperature controller 11 may include at least one of a refrigerant cycle device 13 and/or a heater 14. However, embodiments are not limited thereto. For example, the temperature controller 11 may include a thermoelement (TEM).

The refrigerant cycle device 13 may control the temperature of the fermentation tank 112 to cool a temperature of the fermentation tank 112. The refrigerant cycle device 13 may include a compressor, a condenser, an expansion mechanism, and the evaporator 134.

The evaporator 134 may contact the outer circumferential surface of the fermentation tank 112. The evaporator 134 may be provided as an evaporation tube wound around the outer circumferential surface of the fermentation tank 112. The evaporator 134 may be accommodated between the fermentation tank 112 and the insulation to cool the fermentation tank 112 insulated by the insulation.

The temperature controller 11 may further include heater 14 that heats the fermentation tank 112. The heater 14 may contact the outer bottom surface of the fermentation tank 112. The heater 14 may be provided as a heat generation heater that generates heat when power is applied. The heater 14 may be provided as a plate heater. Thus, natural convection of a fluid may be generated inside of the fermentation tank 112 by the evaporator 134 and the heater 14, and temperature distribution inside of the fermentation tank 112 and the fermentation container 12 may be uniform.

As described above, the main channels 41 and 42 may include first main channel 41 that connects the fluid supply module 5 to the ingredient supplier 3 and second main channel 42 that connects the ingredient supplier 3 to the fermentation module 1. That is, the first main channel 41 may guide a fluid, such as water supplied from the fluid supply module 5 to the ingredient supplier 3, and the second main channel 42 may guide a mixture of ingredients and the fluid, which are extracted from the ingredient supplier 3, to the fermentation module 1.

The first main channel 41 may have a first end 41a connected to the fluid supply module 5 and a second end connected to the ingredient supplier 3, more particularly, an inlet 31a of an initial ingredient receiver 31, which will be described hereinafter.

An ingredient supply valve 310 that opens and closes the first main channel 41 may be installed in the first main channel 41. The ingredient supply valve 310 may be provided in the ingredient supplier 3.

The ingredient supply valve 310 may be opened when additives accommodated in the ingredient receivers 31, 32, and 33 are input to open the first main channel 41. The ingredient supply valve 310 may also be opened when the ingredient receivers 31, 32, and 33 are cleaned to open the first main channel 41.

The second main channel 42 may have a first end connected to the main channel connecting portion 115 of the fermentation module 1 and a second end connected to the ingredient supplier 3, more particularly, an outlet 33b of a final ingredient receiver 33, which will be described hereinafter.

A main valve 40 that opens and closes the second main channel 42 may be installed in the second main channel 42. Also, a main check valve 314 that allows fluid to flow from the ingredient supplier 3 to the fermentation module 1 may be installed in the second main channel 42. That is, the main check valve 314 may prevent the fluid from flowing back to the ingredient supplier 3. The main check valve 314 may be disposed between the main valve 40 and the ingredient supplier 3 with respect to the second main channel 42.

The main valve 40 may be opened to open the second main channel 42 when fluid is supplied to the fermentation container 12. The main valve 40 may be closed to close the second main channel 42 while the fermentation tank 112 is cooled. The main valve 40 may be opened to open the second main channel 42 when air is injected into the fermentation container 12. The main valve 40 may be opened to open the second main channel 42 when ingredients are supplied into the fermentation container 1. The main valve 40 may be closed to seal the inside of the fermentation container 12 during fermentation of the ingredients. The main valve 40 may be closed to seal the inside of the fermentation container 12 when the beverage is aged and stored. The main valve 40 may be opened to open the second main channel 42 when the beverage is dispensed by the beverage dispenser 6. The beverage within the fermentation container 1 may pass through the main valve 40 to flow to the beverage dispenser 6.

The main channels 41 and 42 may be provided as one continuous channel when the beverage maker does not include the ingredient supplier 3. When the beverage maker includes the ingredient supplier 3, the beverage maker may further include bypass channel 43 configured to allow fluid or air to bypass the ingredient receivers 31 and 32.

The bypass channel 43 may bypass the ingredient receivers 31, 32, and 33 and then be connected to the first main channel 41 and the second main channel 42. The bypass channel 43 may have a first end 43a connected to the first main channel 41 and a second end 43b connected to the second main channel 42. The first end 43a of the bypass channel 43 may be connected to the first main channel 41 between the fluid supply module 5 and the ingredient supply valve 310 and the second end 43b may be connected to the second main channel 42 between the main valve 40 and the ingredient supplier 3.

A bypass valve 35 that opens and closes the bypass channel 43 may be installed in the bypass channel 43. The bypass valve 35 may be opened to open the bypass channel 43 when fluid supplied from the fluid supply module 5 is supplied to the fermentation container 12. The bypass valve 35 may be opened to open the bypass channel 43 when air injected from the air injector 8 is supplied to the fermentation container 12. The bypass valve 35 may be opened to open the bypass channel 43 when the bypass channel 43 is cleaned.

A bypass check valve 324 that allows fluid to flow from the first main channel 41 to the second main channel 42 may be installed in the bypass channel 43. That is, the fluid may flow only from the first main channel 41 to the second main channel 42, but may not flow in the opposite direction. The bypass check valve 324 may be disposed between the bypass valve 35 and the second main channel 42 with respect to the bypass channel 43.

When beer is made using the beverage maker, ingredients for making the beer may include water, malt, yeast, hop, and flavoring additives, for example. The beverage maker may include all of the ingredient supplier 3 and the fermentation container 12. The ingredients for making the beverage may be accommodated separately in the ingredient supplier 3 and the fermentation container 12. That is, a portion of the ingredients for making the beverage may be accommodated in the fermentation container 12, and the remaining ingredients may be accommodated in the ingredient supplier 3. The remaining ingredients accommodated in the ingredient supplier 3 may be supplied to the fermentation container 12 together with the fluid supplied from the fluid supply module 5 and mixed with the portion of the ingredients accommodated in the fermentation container 12.

A main ingredient that is essential for making a beverage may be accommodated in the fermentation container 12, and the other ingredients or additives added to the main ingredient may be accommodated in the ingredient supplier 3. In this case, the additives accommodated in the ingredient supplier 3 may be mixed with fluid supplied from the fluid supply module 5 and supplied to the fermentation container 12 and then mixed with the main ingredient accommodated in the fermentation container 12.

An amount of the main ingredient accommodated in the fermentation container 12 may be greater than an amount of other ingredients. For example, when beer is made, the main material may be malt of malt, yeast, hop, and flavoring additives. Also, the additive accommodated in the ingredient supplier 3 may be the other ingredients except for the malt of the ingredients for making beer, for example, yeast, hop, and flavoring additives.

According to one embodiment, beverage maker may not include the ingredient supplier 3 but may include the fermentation container 12. In this case, the main ingredient may be accommodated in the fermentation container 12, and the user may directly put the additives into the fermentation container 12.

If the beverage maker includes both the ingredient supplier 3 and the fermentation container 12, the beverage may be more easily made. Hereinafter, a case in which the beverage maker includes both the ingredient supplier 3 and the fermentation container 12, will be described as an example. However, embodiments are not limited to the case in which the beverage maker includes both the ingredient supplier 3 and the fermentation container 12.

The ingredients within the fermentation container 12 may be fermented over time, and the beverage made in the fermentation container 12 may flow to the second main channel 42 through the main channel connecting portion 115 and also flow from the second main channel 42 to the beverage dispenser 6 to be dispensed.

The ingredients that are necessary for making the beverage may be accommodated in the ingredient supplier 3, and the fluid supplied from the fluid supply module 5 may pass through ingredient supplier 3. For example, when the beverage made in the beverage maker is beer, the ingredients accommodated in the ingredient supplier 3 may be yeast, hop, and flavoring additives, for example.

The ingredients accommodated in the ingredient supplier 3 may be directly accommodated into the ingredient receivers 31, 32, and 33 provided in the ingredient supplier 3. At least one ingredient receiver 31, 32, and 33 may be provided in the ingredient supplier 3. Also, a plurality of ingredient receivers 31, 32, and 33 may be provided in the ingredient supplier 3. The plurality of ingredient receivers 31, 32, and 33 may be partitioned with respect to each other.

Inlets 31a, 32a, and 33a, through which the fluid may be introduced, and outlets 31b, 32b, and 33b, through which the fluid may be discharged, may be provided in the ingredient receivers 31, 32, and 33, respectively. The fluid introduced into the inlet of one ingredient receiver may be mixed with the ingredients within the ingredient receivers and then discharged through the outlet.

The ingredients accommodated in the ingredient supplier 3 may be accommodated in ingredient containers C1, C2, and C3. The ingredient containers C1, C2, and C3 may be accommodated in the ingredient receivers 31, 32, and 33, and each of the ingredient receivers 31, 32, and 33 may be referred to as an ingredient container mount. The ingredient containers C1, C2, and C3 may be a capsule, or a pod, for example; however, embodiments are not limited thereto.

When the ingredients are accommodated in the ingredient containers C1, C2, and C3, the ingredient supplier 3 may be configured so that the ingredient containers C1, C2, and C3 may be seated therein and withdrawn therefrom. The ingredient supplier 3 may be provided as an ingredient container kit assembly in which the ingredient containers C1, C2, and C3 are separably accommodated.

For example, a first additive, a second additive, and a third additive may be accommodated in the ingredient supplier 3. The first additive may be yeast, the second additive may be hop, and the third additive may be a flavoring additive. The ingredient supplier 3 may include a first ingredient container mount 31 in which a first ingredient container C1 containing the first additive may be accommodated, a second ingredient container mount 32 in which a second ingredient container C2 containing the second additive may be accommodated, and a third ingredient container mount 33 in which a third ingredient container C3 containing the third additive may be accommodated.

The ingredients contained in the ingredient receivers or the ingredient containers C1, C2, and C3 may be extracted by a fluid pressure of fluid supplied from the fluid supply module 5. When the ingredients are extracted by the fluid pressure, the fluid supplied from the fluid supply module 5 to the first main channel 41 may pass through the ingredient receivers or the ingredient containers C1, C2, and C3 and then may be mixed with the ingredients, and the ingredients accommodated in the ingredient receivers or the ingredient containers C1, C2, and C3 may flow to the second main channel together with the fluid.

A plurality of different additives may be accommodated separately in the ingredient supplier 3. For example, when beer is made, the plurality of additives accommodated in the ingredient supplier 3 may be yeast, hop, and a flavoring additive, which may be accommodated separated from each other.

When the plurality of ingredient receivers is provided in the ingredient supplier 3, the plurality of ingredient receivers 31, 32, and 33 may be connected in series to each other in a flow direction of the fluid. That is, the ingredient supplier 3 may include at least one connecting channel 311 and 312 that connects the outlet of one ingredient receiver of the plurality of ingredient receivers 31, 32, and 33 to the inlet of another ingredient receiver.

Also, the plurality of ingredient receivers 31, 32, and 33 may include an initial ingredient receiver 31 and a final ingredient receiver 33. The plurality of ingredient receivers 31, 32, and 33 may further include an intermediate ingredient receiver 32.

The inlet 31a of the initial ingredient receiver 31 may be connected to the first main channel 41, and the outlet 33b of the final ingredient receiver 33 may be connected to the second main channel 42. The intermediate ingredient receiver 32 may be disposed between the first ingredient receiver 31 and the second ingredient receiver 33 in the flow direction of the fluid. The inlet 32a and the outlet 32b of the intermediate ingredient receiver 32 may be connected to different connecting channels 311 and 312 from each other.

As illustrated in FIG. 1, when three ingredient receivers are provided in the ingredient supplier 3, the outlet 31b of the initial ingredient receiver 31 may be connected to the inlet 32a of the intermediate ingredient receiver 32 through the first connecting channel 311, and the outlet 32b of the intermediate ingredient receiver 32 may be connected to the inlet 33a of the final ingredient receiver 33 through the second connecting channel 312. The fluid introduced into the inlet 31a of the final ingredient receiver 31 through the first main channel 41 may flow to the first connecting channel 311 through the outlet 31b together with the first additive accommodated in the initial ingredient receiver 31.

The fluid, which may be a mixture of water and a first additive, introduced into the inlet 32a of the intermediate ingredient receiver 32 through the first main channel 311 may flow to the second connecting channel 312 through the outlet 32b together with the second additive accommodated in the intermediate ingredient receiver 32. The fluid, which may now be a mixture of water and first and second additives, introduced into the inlet 33a of the final ingredient receiver 33 through the second main channel 312 may flow to the second connecting channel 42 through the outlet 33b together with a third additive accommodated in the final ingredient receiver 33. The fluid, which may now be a mixture of water and first, second, and third additives, discharged through the second main channel 42 may be guided to the main channel connecting portion 115 of the fermentation module 1 and then introduced into the fermentation container 12.

However, the configuration of the ingredient supplier is not limited thereto. For example, when the intermediate ingredient receiver is not provided, two ingredient receivers may be provided in the ingredient supplier 3. In this case, one ingredient receiver may be the initial ingredient receiver, and the other ingredient receiver may be the final ingredient receiver. The outlet of the initial ingredient receiver and the inlet of the final ingredient receiver may be connected to each other by the connecting channel.

For another example, when a plurality of the intermediate ingredient receiver is provided, four or more ingredient receivers may be provided in the ingredient supplier 3. In this case, one ingredient receiver may be the initial ingredient receiver, another ingredient receiver may be the final ingredient receiver, and the remaining ingredient receiver may be the intermediate ingredient receiver. In this case, as the connection between the ingredient receivers in series is easily understood by a person skilled in the art, detailed descriptions thereof have been omitted.

As the plurality of ingredient receivers 31, 32, and 33 may be connected in series to each other, the channel configuration of the ingredient supplier 3 may be simplified. Further, as the additives contained in the ingredient containers C1, C2, and C3 may be extracted all at once, a time taken to extract the additives may decrease. Furthermore, as the user does not have to worry about a mounting order of the ingredient containers C1, C2, and C3, malfunction due to the mounting of the ingredient containers C1, C2, and C3 in an erroneous order may not occur. Also, fluid leakage in the ingredient supplier 3 may be minimized to improve reliability.

When the ingredients accommodated in the ingredient supplier 3 are accommodated in the ingredient containers C1, C2, and C3, the initial ingredient receiver 31 may be referred to as "an initial ingredient container mount", the intermediate ingredient receiver 32 may be referred to as an "intermediate ingredient container mount", and the final ingredient receiver 33 may be referred to as a "final ingredient container mount".

The fluid supply module 5 may include a tank 51, a pump 52 that pumps a fluid, such as water within the tank 51, and a heater 53 that heats the fluid pumped by the pump 52. The tank 51 and the pump 52 may be connected to a tank discharge channel 55a, and the fluid contained in the tank 51 may be introduced into the pump 52 through the tank discharge channel 55a.

The pump 52 and a first end of the first main channel 41 may be connected to a supply channel 55b, and the fluid discharged from the pump 52 may be guided to the first main channel 41 through the supply channel 55b. A flow meter 56 that measures a flow rate of the fluid discharged from the tank 51 may be installed in the tank discharge channel 55a.

A flow rate control valve 54 that controls a flow rate of the fluid discharged from the tank 51 may be installed in the tank discharge channel 55a. The flow rate control valve 54 may include a step motor.

A thermistor 54a that measures a temperature of the fluid discharged from the tank 51 may be installed in the tank discharge channel 55a. The thermistor 54a may be built into the flow rate control valve 54.

A check valve 59 that prevents the fluid from flowing back to the pump 52 may be installed in the supply channel 55b. Also, the heater 53 may be installed in the supply channel 55b. A thermal fuse 58 that interrupts a circuit to cutoff current applied to the heater 53 when a temperature is high may be installed in the heater 53.

The fluid supply module 5 may further include a safety valve 53a. The safety valve 53a may communicate with an inside of a heater case of the heater 53. The safety valve 53a may restrict a maximum inner pressure of the heater case. For example, the safety valve 53a may restrict the maximum inner pressure of the heater case to a pressure of about 3.0 bar.

The fluid supply module 5 may further include a temperature sensor 57 that measures a temperature of the fluid passing through the heater 53. The temperature sensor 57 may be installed in the heater 53. Alternatively, the temperature sensor 57 may be disposed at a portion of the supply channel 55b behind the heater 53 in the flow direction of fluid. Also, the temperature sensor 57 may be installed in the first main channel 41.

When the pump 52 is driven, the fluid within the tank 51 may be introduced into the pump 52 through the tank discharge channel 55a, and the fluid discharged from the pump 52 may be heated in the heater 53 while flowing through the supply channel 55b and then be guided to the first main channel 41.

The beverage dispenser 6 may be connected to the second main channel 42. The beverage dispenser 6 may include the dispenser 62 that dispenses a finished beverage and the beverage dispensing channel 61 that connects to the dispenser 62 to the second main channel 42.

The beverage dispensing channel 61 may have a first end 61a connected between the main check valve 314 and the main valve 40 with respect to the second main channel 42 and a second end connected to the dispenser 62. A beverage dispensing valve 64 that opens and closes the beverage dispensing channel 61 may be installed in the beverage dispensing channel 61.

The beverage dispensing valve 64 may be opened to open the beverage dispensing channel 61 when the beverage is dispensed. The beverage dispensing valve 64 may be opened to open the beverage dispensing channel 61 when residual fluid is removed. The beverage dispensing valve 64 may be opened to open the beverage dispensing channel 61 when the beverage dispenser is cleaned.

An anti-foaming portion (not shown) may be provided in the beverage dispensing channel 61, and an amount of foam of the beverage flowing from the second main passage 42 to the beverage dispensing channel 61 may be minimized while passing through the anti-foaming portion. A mesh that filters the foam may be provided in the anti-foaming portion (not shown).

When the beverage is dispensed, the beverage dispensing valve 64 may be opened. When the beverage is not dispensed, the beverage dispensing valve 64 may be maintained in a closed state.

The gas discharger 7 may be connected to the fermentation module 1 to discharge gas generated in the fermentation container 12. The gas discharger 7 may include a gas discharge channel 71 connected to the fermentation module 1, a gas pressure sensor 72 installed in the gas discharge channel 71, and a gas discharge valve 73 connected upstream of the gas pressure sensor 72 in the gas discharge channel 71 in a gas discharge direction.

The gas discharge channel 71 may be connected to the fermentation module 1, more particularly, the fermentation lid 107. A gas discharge channel connecting portion 121 to which the gas discharge channel 71 may be connected may be provided in the fermentation lid 107.

The gas within the fermentation container 12 may flow into the gas discharge channel 71 and the gas pressure sensor 72 through the gas discharge channel connecting portion 121. The gas pressure sensor 72 may detect a pressure of the gas discharged to the gas discharge channel 71 through the gas discharge channel connecting portion 121 within the fermentation container 12.

The gas discharge valve 73 may be opened when the air is injected into the fermentation container 12 by the air injector 8. The beverage maker may uniformly mix the malt with the fluid by injecting air into the fermentation container 12. Foam generated in the liquid malt may be discharged from an upper portion of the fermentation container 12 to the outside through the gas discharge channel 71 and the gas discharge valve 73. The gas discharge valve 73 may be opened during the fermentation process and then closed.

The gas discharger 7 may further include a safety valve 75 connected to the gas discharge channel 71. The safety valve 75 may be connected upstream of the gas pressure sensor 71 in the gas discharge channel 71 in the gas discharge direction. The safety valve 75 may restrict a maximum pressure of the fermentation container 12 and the gas discharge channel 71. For example, the safety valve 75 may restrict the maximum pressure of the fermentation container 12 and the gas discharge channel 71 to a pressure of about 3.0 bar.

The gas discharger 7 may further include a pressure release valve 76. The pressure release valve 76 may be connected to the gas discharge channel 71. The pressure release valve 76 and the gas discharge valve 73 may be selectively opened/closed. The gas discharge channel 71 may be branched to be respectively connected to the gas discharge valve 73 and the pressure release valve 76.

A noise reducing device 77 may be mounted on the pressure release valve 76. The noise reducing device 77 may include at least one of an orifice structure or a muffler structure, for example.

Even though the pressure release valve 76 is opened, an inner pressure of the fermentation container 12 may gradually decrease due to the noise reducing device 77. When fermentation of the beverage progresses, the pressure release valve 76 may be opened to release the pressure in a state in which the inner pressure of the fermentation container 12 increases. The noise reducing device 77 may effectively reduce noise generated due to a difference in pressure between the inside and outside of the fermentation container 12. The pressure release valve 76 may be open/close-controlled in a fermentation operation with relatively high internal pressure.

The air injector 8 may be connected to the supply channel 55b or the first main channel 41 to inject air. Hereinafter, for convenience of description, a case in which the air injector 8 is connected to the supply channel 55b will be described as an example.

The air injector 8 may be connected to an opposite side of a sub channel 91, which will be described hereinafter, with respect to the heater 53. The air injected by the air injector 8 may pass through the heater 53 to flow to the sub channel 91 together with residual fluid within the heater 53. Thus, the residual fluid within the heater 53 may be removed to maintain a clean state of the heater 53.

Alternatively, air injected from the air injector 8 to the first main channel 41 may successively pass through the bypass channel 43 and the second main channel 42 and then be injected into the fermentation container 12. Thus, stirring or aeration may be performed in the fermentation container 12.

Alternatively, air injected from the air injector 8 to the first main channel 41 may be guided to the ingredient supplier 3 to flow to the ingredient container mounts 31, 32, and 33. Residual fluid or residue within the ingredient containers C1, C2, and C3 or the ingredient container mounts 31, 32, and 33 may flow to the second main channel 42 due to air injected by the air injector 8. The ingredient containers C1, C2, and C3 and the ingredient container mounts 31, 32, and 33 may be cleanly maintained by the air injected by the air injector 8.

The air injector 8 may include an air injection channel 81 connected to the supply channel 55b or the first main channel 41 and an air pump 82 connected to the air injection channel 81. The air pump 82 may pump air to the air injection channel 81. An air injection check valve 83 that prevents fluid flowing to the supply channel 55b by the pump 52 from being introduced into the air pump 82 through the air injection channel 81 may be installed in the air injection channel 81.

The air injector 8 may further include an air filter 82a. The air filter 82a may be provided in a suction portion of the air pump 82, and thus, external air may be suctioned into the air pump 82 by passing through the air filter 82a. Thus, the air pump 82 may inject clean air into the air injection channel 81.

The air controller 15 may control a pressure between the inner wall of the fermentation tank 112 and the outer surface of the fermentation container 12. The air controller 15 may supply air into a space between the fermentation container 12 and the fermentation tank 112. On the other hand, the air controller 15 may exhaust the air within the space between the fermentation container 12 and the fermentation tank 112 to the outside.

The air controller 15 may include an air supply channel 154 connected to the fermentation module 1, and an exhaust channel 157 connected to the air supply channel 154 to exhaust the air to the outside. The air supply channel 154 may have a first end connected to the first main channel 41 and a second end connected to the fermentation module 1.

The air supply channel 154 may be connected to the fermentation module 1, more particularly, the fermentation lid 107. An air supply channel connecting portion 117 to which the air supply channel 154 may be connected may be provided in the fermentation module 1. The air supply channel connecting portion 117 may communicate with the space between the inner wall of the fermentation tank 112 and the outer surface of the fermentation container 12.

The air injected from the air injector 8 to the first main channel 41 may be guided between the outer surface of the fermentation container 12 and the inner wall of the fermentation tank 112 through the air supply channel 154. The air injector 8 may function as an air supplier that supplies air into the space between the fermentation container 12 and the fermentation tank 112 together with the air supply channel 154.

As described above, the air supplied into the fermentation tank 112 may press the fermentation container 12 between the outer surface of the fermentation container 12 and the inner wall of the fermentation tank 112. The beverage within the fermentation container 12 may be pressed by the fermentation container 12 pressed by the air. When the main valve 40 and the beverage dispensing valve 64 are opened, the beverage may pass through the main channel connecting portion 115 to flow to the second main channel 42. The beverage flowing from the fermentation container 12 to the second main channel 42 may be dispensed to the outside through the beverage dispenser 6.

The air pump 82 may supply air so that a predetermined pressure occurs between the fermentation container 12 and the fermentation tank 112. Thus, a pressure at which the beverage within the fermentation container 12 is easily dispensed may occur between the fermentation container 12 and the fermentation tank 112.

The air pump 82 may be maintained in an off state while the beverage is dispensed. When the beverage is completely dispensed, the air pump 82 may be driven for a next beverage dispensing and then stopped.

Thus, when the beverage is finished, the beverage maker may dispense the beverage within the fermentation container 12 to the beverage dispenser 6 in a state in which the fermentation container 1 is disposed within the fermentation module 1 without withdrawing the fermentation container 12 to the outside of the fermentation module 1.

The air controller 15 may include a separate air supply pump with respect to the air injector 8. In this case, the air supply channel 154 may be connected to the air supply pump, but may not be connected to the first main channel 41. However, the injection of air into the fermentation container 12 by the air pump 82 and the supplying of air into the space between the fermentation container 12 and the fermentation tank 112 may be combined with each other to realize a compact product and reduce manufacturing costs.

The exhaust channel 157 may function as an air exhaust passage, through which the air between the fermentation container 12 and the fermentation tank 112 may be exhausted to the outside, together with a portion of the air supply channel 154. The exhaust channel 157 may be disposed outside of the fermentation module 1. The exhaust channel 157 may be connected to a portion of the air supply channel 154, which is disposed outside of the fermentation tank 112.

The air supply channel 154 may include a first channel connected between a connecting portion 157a connected to the first main channel 41 and the exhaust channel 157 and a second channel connected between the connecting portion 154a connected to the exhaust channel 157 and the air supply channel connecting portion 117. The first channel may be an air supply channel that guides the air pumped by the air pump 82 to the second channel. Also, the second channel may be an air supply and exhaust-combined channel that supplies the air passing through the air supply channel into the space between the fermentation tank 112 and the fermentation container 12 or guides the air discharged from the space between the fermentation tank 112 and the fermentation container 12 the connecting channel 157.

The exhaust channel 157 may be connected to the exhaust valve 156 that opens and closes the exhaust channel 157. The exhaust valve 156 may be opened so that the air between the fermentation container 12 and the fermentation tank 112 may be exhausted to the outside when the fermentation container 12 is expanded while the beverage is made. The exhaust valve 156 may be opened when the fluid is supplied by the fluid supply module 5. The exhaust valve 156 may be opened when the air is injected by the air injector 8.

The exhaust valve 156 may be opened so that the air between the fermentation container 12 and the fermentation tank 112 is exhausted when the beverage within the fermentation container 12 is completely dispensed. The user may take the fermentation container 12 out of the fermentation tank 112 when the beverage is completely dispensed. This is done because safety accidents occur when the inside of the fermentation tank 112 is maintained at a high pressure. The exhaust valve 156 may be opened when the beverage within the fermentation container 12 is completely dispensed.

The air controller 15 may further include an air supply valve 159 that restricts the air pumped by the air pump 82 and supplied between the fermentation container 12 and the fermentation tank 112. The air supply valve 159 may be installed in the air supply channel 154. That is, the air supply valve 159 may be installed between the connecting portion 154a of the first main channel 41 and the connecting portion 157a of the exhaust channel 157 in the air supply channel 154.

The sub channel 91 may connect the fluid supply module 5 to the beverage dispenser 6. That is, the sub channel 91 may have a first end 91a connected to the supply channel 55b and a second end 91b connected to the beverage dispensing channel 61.

The sub channel 91 may be connected between the pump 52 and the heater 53 with respect to the supply channel 55b. Also, the sub channel 91 may be connected to the connecting portion 61a of the second main channel 42 and the beverage dispensing valve 64 with respect to the beverage dispensing channel 61.

The fluid supplied by the pump 52 and the air pumped by the air pump 82 may be guided to the beverage dispensing channel 61 through the sub channel 91 and then may be dispensed to the dispenser 62. Thus, residual fluid or beverage remaining in the beverage dispenser 6 may be removed.

A sub valve 92 that opens and closes the sub channel 91 may be installed in the sub channel 91. The sub valve 92 may be opened to open the sub channel 91 when the beverage is dispensed, or cleaning is performed.

A sub check valve 93 that prevents the beverage in the beverage dispensing channel 61 from flowing back to the fluid supply module 5 may be installed in the sub channel 91. The sub check valve 93 may be disposed between the sub valve 92 and the beverage dispensing channel 61 with respect to the sub channel 91.

The sub channel 91 may function as a residual fluid removing channel of the fluid supply module 5. For example, when the air pump 82 is turned on in a state in which the air supply valve 159, the bypass valve 35, and the ingredient supply valve 310 are closed, the sub valve 92 is opened, and the air injected into the air injection channel 81 may pass through the heater 53 to flow to the sub channel 91. Then, the air may pass through the sub valve 92 to flow to the beverage dispensing channel 61 and then be dispensed to the dispenser 62. In this process, the air may be dispensed together with fluid from the fluid supply module 5, more particularly, the residual fluid remaining in the heater 53 and the supply channel 55*b* so that residual fluid may be removed.

The sub channel 91 may function as a cleaning channel. That is, a beverage may be partially dispensed by the dispenser 62, and when a long period of time has elapsed before a next beverage dispensing, fluid may flow to the sub channel 91 to clean the dispenser 62 before the next beverage dispensing is performed.

FIG. 2 is a flowchart of an operation for making a beverage in a beverage maker according to an embodiment. In the following drawing, although a case in which a beverage made by the beverage maker is beer will be exemplified, the type of beverage to be made by the beverage maker according to an embodiment is not limited to beer.

Hereinafter, an operation for making a beverage in a beverage maker according to an embodiment will be described with reference to FIG. 2 in addition to FIG. 1.

In order to make a beverage, a user may open the fermentation lid 107 and may insert the fermentation container 12 into the fermentation module 1. Some ingredients, for example, malt, may be accommodated in the fermentation container 12. The malt may be accommodated in the form of barley malt. According to an embodiment in which the fermentation container 12 is not embodied, the user may introduce some ingredients directly into the fermentation tank 112 of the fermentation module 1.

Then, the user may close the fermentation lid 107, and fermentation container 12 may be accommodated in the fermentation module 1. In this case, an internal portion of the fermentation module 1 may be closed by the fermentation lid 107.

The user may insert the ingredient containers C1, C2, and C3 into the ingredient receivers 31, 32, and 33 before or after the fermentation container 12 is inserted. The user may input a command for making a beverage through an input interface 420 (see FIG. 3), a remote controller, or a mobile terminal, for example. A controller 440 (see FIG. 3) may control the beverage maker to perform a beverage making operation according to the command for making a beverage.

The beverage making operation may include a hot fluid supply operation (S100). The hot fluid supply operation (S100) may be a liquid malt operation of uniformly mixing malt in the fermentation container 12 with a hot fluid, such as water to form liquid malt.

In the hot fluid supply operation (S100), the controller 440 may turn on the pump 52 and may introduce a fluid, such as water from the tank 51 into the fermentation container 12. In some embodiments, in order to introduce hot fluid into the fermentation container 12, the fluid supply module 5 may further include heater 53. In this case, fluid output from the tank 51 may pass through the pump 52, may flow to the heater 53, and may be heated by the heater 53. Fluid, such as water (=hot water) heated by the heater 53 may flow into the fermentation container 12 through channels 55*b*, 41, 43, and 42 between the fluid supply module 5 and the fermentation module 1. The hot fluid introduced to the fermentation container 12 may be mixed with malt accommodated in the fermentation container 12, and malt inside the fermentation container 12 may be mixed with fluid and may be gradually diluted. The hot fluid may be supplied to the fermentation container 12, and thus, malt accommodated in the fermentation container 12 may be rapidly and uniformly mixed with hot fluid.

The controller 440 may perform the hot fluid supply operation (S100) until a cumulative fluid volume detected by the flow meter 56 included in the fluid supply module 5 reaches a set or predetermined flow rate, and may complete the hot fluid supply operation (S100) when the cumulative fluid volume detected by the flow meter 56 reaches the set flow rate. When the hot fluid supply operation (S100) is completed, the controller 440 may turn off the pump 52 and the heater 53.

During the hot fluid supply operation S100, the controller 440 may control the air pump 82 to introduce air into the fermentation container 12. When air is introduced, malt and hot fluid of the fermentation container 12 may be more smoothly mixed with each other.

The controller 440 may primarily introduce a fluid, such as water into the fermentation container 12 and may stop the primary introduction, may then inject air into the fermentation container 12, and lastly, may secondarily introduce a hot fluid, such as water into the fermentation container 12 and may stop the secondary introduction. The hot fluid supply operation (S100) may be completed after sequentially completing the primary introduction of fluid, the injection of air, and the secondary introduction of fluid.

As an example of the hot fluid supply operation (S100), only a hot fluid supply operation of supplying hot fluid may be performed. In another example of the fluid water supply operation (S100), a primary hot fluid supply operation of primarily supplying hot fluid, an air injection procedure of injecting air, and a secondary hot fluid supply operation of secondarily supplying hot fluid may be sequentially performed.

The beverage making operation may further include a fermentation module cooling operation (S110). That is, when the hot fluid supply operation (S100) is completed, the fermentation module cooling operation (S110) of cooling the fermentation tank 112 or the fermentation container 12 of the fermentation module 1 may be performed.

The controller 440 may control the temperature controller 11 included in the fermentation module 1 in order to cool the fermentation container 12. That is, the controller 440 may control the refrigerant cycle device 13 in order to cool the fermentation container 12. When the refrigerant cycle device 13 is driven, the fermentation container 12 may be gradually cooled, and a mixture (liquid malt) of fluid, such as water and malt accommodated in the fermentation container 12 may be cooled. The controller 440 may control the refrigerant cycle device 13 depending on a temperature detected by the temperature sensor 16 installed in the fermentation module 1. For example, when the temperature detected by the temperature sensor 16 reaches a set or predetermined cooling operation temperature, the controller 440 may turn off the refrigerant cycle device 13.

The beverage making operation may include an air supply and additives introduction operation (S120). The air supply and additives introduction operation (S120) may be performed during the fermentation module cooling operation (S110) or may be performed after the fermentation module cooling operation (S110) is completed.

In an air supply operation of the air supply and additives introduction operation (S120), the controller 440 may turn on the air pump 82. While the air pump 82 is turned on, air may pass through a channel between the air pump 82 and the fermentation module 1 and may be introduced into the fermentation container 12. As such, air introduced into the fermentation container 12 may collide with liquid malt to facilitate uniform mixing between malt and hot water, and the air colliding with the liquid malt may supply oxygen to the liquid malt to increase dissolved oxygen (DO) of the liquid malt. That is, agitation and aeration may be performed. As dissolved oxygen (DO) of liquid malt increases, yeast included in additives introduced to the fermentation container 12 may more effectively function, and thus, fermentation of beverage may be smoothly performed.

The controller 440 may turn on the air pump 82 for a predetermined period of time and may supply air into the fermentation container 12. When the predetermined period of time has elapsed, the controller 440 may turn off the air pump 82 to complete the air supply operation.

The beverage maker may then perform an additives introduction operation of the air supply and additives introduction operation (S120). During the additives introduction operation, additives accommodated in the ingredient supplier 3 may be introduced into the fermentation container 12.

During the additives introduction operation, the controller 440 may turn on the pump 52. When the pump 52 is turned on, a fluid, such as water of the tank 51 may pass through a channel between the pump 52 and the fluid supply module 5 and the ingredient supplier 3 and may be introduced into the ingredient containers C1, C2, and C3 in the ingredient supplier 3. The fluid introduced into the ingredient containers C1, C2, and C3 may be mixed with additives accommodated in the ingredient containers C1, C2, and C3 and may be introduced into the fermentation container 12 along with the additives.

When a cumulative flow rate detected by the flow meter 56 reaches a predetermined flow rate after the additives introduction operation begins, the controller 440 may complete the additives introduction operation. When the additives introduction operation is completed, the controller 440 may turn off the pump 52.

When the air supply and additives introduction operation (S120) is completed, the controller 440 may display an ingredient container removal message indicating that the ingredient containers C1, C2, and C3 may be removed, on a display 132 (see FIG. 3), and a user may remove an empty ingredient container from the ingredient supplier 3.

The beverage making operation may include a fermentation operation (S130). For example, the fermentation operation (S130) may include a primary fermentation operation and a secondary fermentation operation.

The controller 440 may control the thermostat 11 to maintain a temperature measured by the temperature sensor 16 at a primary fermentation target temperature, for example, 21° C., during the primary fermentation operation.

The controller 440 may periodically open and close the gas discharge valve 73 or the pressure release valve 76 of the gas discharger 7 and may store a pressure detected by the gas pressure sensor 72 included in the gas discharger 7 while the gas discharge valve 73 is closed, in a memory 430 (see FIG. 3). When a change in pressure periodically detected by the gas pressure sensor 72 is greater than a primary fermentation pressure, the controller 440 may complete the primary fermentation operation.

After completing the primary fermentation operation, the controller 440 may initiate the secondary fermentation operation. During the secondary fermentation operation, the controller 440 may control the thermostat 11 in such a way that a temperature measured by the temperature sensor 16 reaches a secondary fermentation target temperature.

After initiating the secondary fermentation operation, the controller 440 may periodically open and close the gas discharge valve 73 of the gas discharger 7, and the controller 440 may store a pressure detected by the gas pressure sensor 72 while the gas discharge valve 73 is closed, in the memory 430. When a change in the pressure periodically detected by the gas pressure sensor 72 is greater than the secondary fermentation target pressure, the controller 440 may determine that the secondary fermentation operation is completed.

The beverage making operation may include an aging operation (S140). That is, when the fermentation operation (S130) is completed, the aging operation (S140) may be performed.

In the aging operation, the controller 440 may be on standby for an aging time and may control the thermostat 11 to maintain a temperature of the beverage for the aging time between an upper limit and a lower limit of a predetermined aging temperature.

When the aging time has elapsed, the beverage may be finished. However, as necessary, the aging operation (S140) may be omitted, and when the fermentation operation (S130) is completed, the beverage may be deemed finished.

The controller 440 may display information indicating that a beverage is completely finished, through the display 132, for example. The controller 440 may control the thermostat 11 to maintain the temperature of the fermentation tank 112 or the fermentation container 12 between an upper limit and a lower limit of a predetermined drinking temperature until a beverage dispensing operation (S150) to be described hereinafter is completed.

The beverage maker according to an embodiment may further include the beverage dispensing operation (S150) for dispensing the beverage after the beverage is completely finished. During the beverage dispensing operation (S150), a user may dispense the beverage by manipulating a lever 620 of the dispenser 62. When the user opens the dispenser 62, the beverage in the fermentation container 12 may pass through a channel between the fermentation module 1 and the dispenser 62 and may be dispensed to the outside.

The user may dispense the beverage through the dispenser 62 at least once. That is, the beverage dispensing operation may be performed at least once, and the controller 440 may determine whether the beverage is completely dispensed using information, such as a time of opening the dispenser 62.

Although not shown, the beverage maker may perform a cleaning operation of washing and sterilizing internal channels before the supply hot fluid operation (S100) is performed or after the beverage dispensing operation (S150) is performed. The cleaning operation may be performed according to user input, for example, while the beverage making operation is performed, and may be performed while the main valve 40 is closed and additives are not accommodated in the ingredient supplier 3, like in a fermentation operation described hereinafter.

FIG. 3 is a schematic block diagram showing control components of a beverage maker according to an embodiment. Referring to FIG. 3, the beverage maker may include a communication interface 410, the input interface 420, the memory 430, and the controller 440. All of the control components shown in FIG. 3 are not a requirement for embodying the beverage maker, and thus, in some embodiments, the beverage maker may include greater or fewer components.

The beverage maker may include the communication interface 410 to communicate with a terminal, such as a smart phone, or a tablet PC, for example, or a server, for example. For example, the controller 440 may receive a request for execution of a function of making a beverage, or recipe information, for example, from a user terminal through the communication interface 410. The controller 440 may transmit various pieces of information, such as a beverage making operation, a making state, or a storage state of a beverage to a terminal or a server through the communication interface 410.

The communication interface 410 may include a module for supporting at least one of pre-known wired or wireless communication methods. For example, the communication interface 410 may include a short-distance wireless communication module, such as Bluetooth or near file communication (NFC), for example, or a wireless Internet module, such as a wireless local area network (WLAN) module, for example.

The input interface 420 may receive various requests or commands from a user. For example, the input interface 420 may include a rotary knob 122, a touch pad 422 (or a touchscreen), other buttons, and/or a microphone, for example. The controller 440 may receive a request for executing a function of making a beverage, recipe information, and/or a control command for other various operations of the beverage maker through the input interface 420.

The display 132 may output various pieces of information related to an operation or state of the beverage maker, and various pieces of information related to a beverage that is being made or stored in the beverage maker. The display 132 may be embodied as a liquid crystal display (LCD), a light emitting diode (LED), and/or an organic light emitting diode (OLED) display, for example. Hereinafter, although the display 132 is assumed to be embodied in a circular shape, embodiments are not limited thereto and a shape of the display 132 may be freely modified.

For example, the display 132 may output information in the form of graphics or text. In some embodiments, the beverage maker may further include a sound output that outputs the information in the form of a voice, and the controller 440 may output the information through various combinations of graphics, text, and voice using the display 132 and the sound output.

The memory 430 may store various pieces of information or data related to an operation of the beverage maker. For example, the memory 430 may store preset recipe information for beverages to be made, various setting values, and/or various program data for an operation of the beverage maker. The memory 430 may store various graphic data related to images displayed through the display 132.

The controller 440 may control an overall operation of the beverage maker. The controller 440 may refer to at least one controller. The at least one controller may be embodied in hardware, such as a CPU, an application processor, a microcomputer (or a micom), an integrated circuit, or an application specific integrated circuit (ASIC), for example.

For example, the controller 440 may control driving of a thermostat (a compressor 131 and/or a heater 14 of the refrigerant cycle device 13) included in the beverage maker, the pump 52, and the air pump 82. In addition, with regard to driving control of the components, the controller 440 may control open/close of valves included in channels. The controller 440 may detect a temperature of the fermentation tank 112 or the fermentation container 12 using the temperature sensor 16 and may control driving components, such as the refrigerant cycle device 13, the heater 14, the pump 52, or the air pump 82, for example, based on the detection result.

FIG. 4 is a flowchart of a cooling operation, an air supply operation, and an additives introduction operation during the beverage making operation described above with reference to FIG. 2.

Referring to FIG. 4, the beverage maker may turn on the refrigerant cycle device 13 included in the thermostat 11 in order to cool a mixture (liquid malt) of malt and hot fluid, such as water (S200). The temperature of the liquid malt may be about 50° C. to 70° C. In contrast, an activation (propagation or growth) degree of yeast included in additives to be added to the liquid malt later may be maximized at about 28° C. to 35° C. In the fermentation operation performed after the additives are introduced, the temperature of the liquid malt may be set to about 21° C. or 12° C. Accordingly, the beverage maker may perform the cooling operation (S110) of lowering the temperature of the liquid malt.

Accordingly, the controller 440 may control the thermostat 11 in order to cool the liquid malt accommodated in the fermentation tank 112 (or the fermentation container 12). That is, the controller 440 may drive the compressor 131 of the refrigerant cycle device 13 included in the thermostat 11. As the compressor 131 is driven, a refrigerant may be supplied to the evaporator 134 wound on an external surface of the fermentation tank 112. The fermentation tank 112 may be cooled by the refrigerant supplied to the evaporator 134. As the fermentation tank 112 is cooled, the fermentation container 12 and liquid malt accommodated in the fermentation tank 112 may also be cooled.

During the cooling operation (S110) along with driving of the refrigerant cycle device 13, the beverage maker may detect the temperature of the fermentation tank 112 or the fermentation container 12 using the temperature sensor 16 (S210). During the cooling operation (S110), the controller 440 may periodically detect the temperature using the temperature sensor 16 included on the external surface of the fermentation tank 112.

As the evaporator 134 is configured to be wound around the external surface of the fermentation tank 112, a temperature of a portion of a surface of the fermentation tank 112, which is adjacent to the evaporator 134, may be cooled to a temperature below zero or close to 0° C., and thus, may have a high difference with the temperature of the liquid malt in the fermentation tank 112. Accordingly, as shown in FIG. 1, the temperature sensor 16 may be spaced apart from the evaporator 134 to more accurately detect the temperature of the liquid malt.

When the detected temperature does not reach a first reference temperature (NO in S220), that is, when the detected temperature is higher than the first reference temperature, the beverage maker may detect a temperature using the temperature sensor 16 until the detected temperature reaches the first reference temperature (or less than the first reference temperature). When the detected temperature reaches the first reference temperature or is less than the first reference temperature (YES in S220), the beverage maker may put additives accommodated in the ingredient supplier 3 into the fermentation tank 112 or the fermentation container 12 (S230).

When the temperature detected by the temperature sensor 16 reaches the first reference temperature or corresponds to a lower temperature than the first reference temperature during the cooling operation (S110), the controller 440 may perform the additives introduction operation described above with reference to FIG. 2. In this case, the cooling operation (S110) may be continuously performed.

The first reference temperature may be a second reference temperature to be described later, for example, about 28° C. to 35° C., for maximizing activation of yeast or a temperature that is higher than the second reference temperature by about 1° C. to 3° C. That is, the additives introduction operation may be performed during the cooling operation (S110), and thus, an entire making time of beverage may be reduced. A control operation of the controller 440 in the additives introduction operation will be described hereinafter with reference to FIG. 9.

The beverage maker may detect a temperature of the fermentation tank 112 or the fermentation container 12 using the temperature sensor 16 (S240). The cooling operation (S110) may be continuously performed while or after the additives introduction operation, and thus, the controller 440 may periodically detect the temperature using the temperature sensor 16.

When the detected temperature does not reach the second reference temperature (NO in S250), that is, when the detected temperature is higher than the second reference temperature, the beverage maker may detect a temperature using the temperature sensor 16 until the detected temperature reaches the second reference temperature (or less than the second reference temperature). When the detected temperature reaches the second reference temperature or is less than the second reference temperature (YES in S250), the beverage maker may turn off the thermostat 11 (the refrigerant cycle device 13) to finish the cooling operation S110 (S260). For example, the second reference temperature may correspond to a temperature, for example, about 28° C. to 35° C., for maximizing activation of yeast.

When the temperature detected by the temperature sensor 16 reaches the second reference temperature, the controller 440 may turn off driving of the compressor 131 included in the refrigerant cycle device 13 to finish the cooling operation (S110). After the refrigerant cycle device 13 is turned off, the beverage maker may perform an air supply operation of supplying air to the fermentation tank 112 or the fermentation container 12 (S270).

As the refrigerant cycle device 13 is turned off, refrigerant supply to the evaporator 134 may be stopped. Accordingly, a temperature of a portion of a surface of the fermentation tank 112, which is adjacent to the evaporator 134, may be gradually increased to the temperature of the liquid malt.

After the refrigerant cycle device 13 is turned off, the controller 440 may control the air pump 82 to supply air to the liquid malt in the fermentation tank 112 or the fermentation container 12. Air supplied to the liquid malt may be dissolved in the liquid malt and the remaining may be discharged to the outside through the gas discharge channel 71. The air discharged to the outside may be discharged above the liquid malt in a state in which the air is contained in a bubble and may be discharged to the outside through the gas discharge channel 71 as the bubble breaks.

Figure 5:
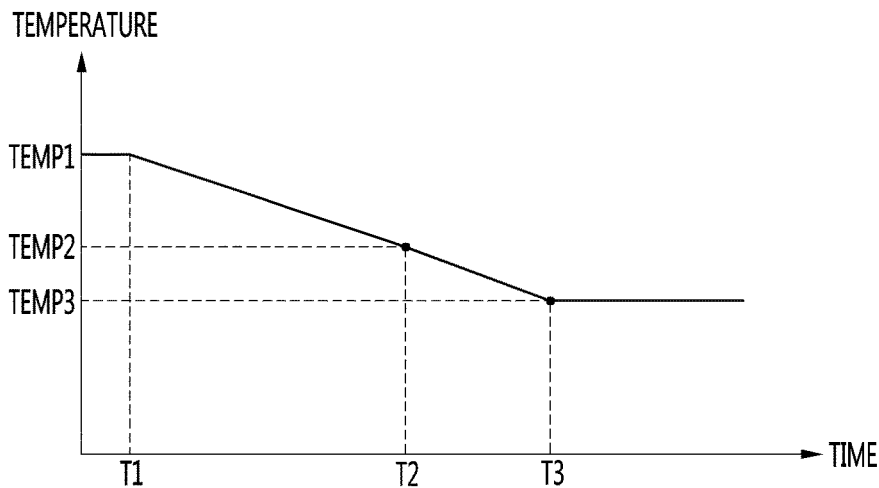
FIG. 5 is a graph showing an example of a temperature change detected by a temperature sensor during an operation of the beverage maker according to the embodiment shown in FIG. 4.

FIG. 5 is a graph showing an example of a temperature change detected by a temperature sensor during an operation of the beverage maker according to the embodiment shown in FIG. 4. Referring to FIG. 5, when hot fluid is supplied to the fermentation tank 112 or the fermentation container 12 in the supply hot fluid operation (S100) of FIG. 2, the temperature detected by the temperature sensor 16 may be a first temperature TEMP1. For example, the first temperature TEMP1 may be about 50° C. to 70° C.

When the hot fluid supply operation (S100) is completed at a first time point T1, the cooling operation (S110) may be performed. As the cooling operation (S110) is performed, the temperature detected by the temperature sensor 16 may be lowered over time.

At a second time point T2 at which the temperature detected by the temperature sensor 16 is a second temperature TEMP2, the beverage maker may perform the additives introduction operation described above in the supply air and introduce additive operation (S120) of FIG. 2 and the put additives into fermentation tank operation (S230) of FIG. 5. That is, the second temperature TEMP2 may correspond to the first reference temperature of FIG. 4. The beverage maker may continuously perform a cooling operation irrespective of the additives introduction operation, and thus, the temperature detected by the temperature sensor 16 may be continuously lowered.

At a third time point T3 at which the temperature detected by the temperature sensor 16 is a third temperature TEMP3, the beverage maker may finish the cooling operation and may perform the air supply operation described above in the supply air and introduce additive operation (S120) of FIG. 2 and supply air into fermentation tank operation (S270) of FIG. 4. That is, the third temperature TEMP3 may correspond to the second reference temperature of FIG. 4.

After the air supply operation is performed for a predetermined period of time, the beverage maker may control the refrigerant cycle device 13 to cool a temperature in the fermentation tank to a fermentation temperature from the third temperature TEMP3. As described above with reference to FIG. 3, as the evaporator 134 is configured to be wound around the external surface of the fermentation tank 112, a temperature of a portion of a surface of the fermentation tank 112, which is adjacent to the evaporator 134, may be cooled to a temperature below zero or close to 0° C., and thus, may have a high difference in temperature with the mixture in the fermentation tank.

When the compressor 131 of the refrigerant cycle device 13 is continuously driven until the temperature in the fermentation tank 112 is cooled to the fermentation temperature, the temperature of the surface of the fermentation tank 112, which is adjacent to the evaporator 134, may be continuously maintained at a temperature below zero or close to 0° C. Accordingly, yeast present at a position adjacent to the fermentation tank 112 around which the evaporator 134 is wound may not be activated, or the activated yeast may not perform fermentation. That is, an activation degree of yeast present in the fermentation tank 112 is degraded, and thus, fermentation of the mixture may not be smoothly performed in the fermentation operation. As a result, a quality or taste of the finished beverage may be degraded, and thus, satisfaction of the user may be degraded.

Hereinafter, an embodiment related to an operation of adjusting a temperature of a mixture in the fermentation tank 112 to the fermentation temperature by the beverage maker will be described with reference to FIGS. 6 to 8.

Figure 6:
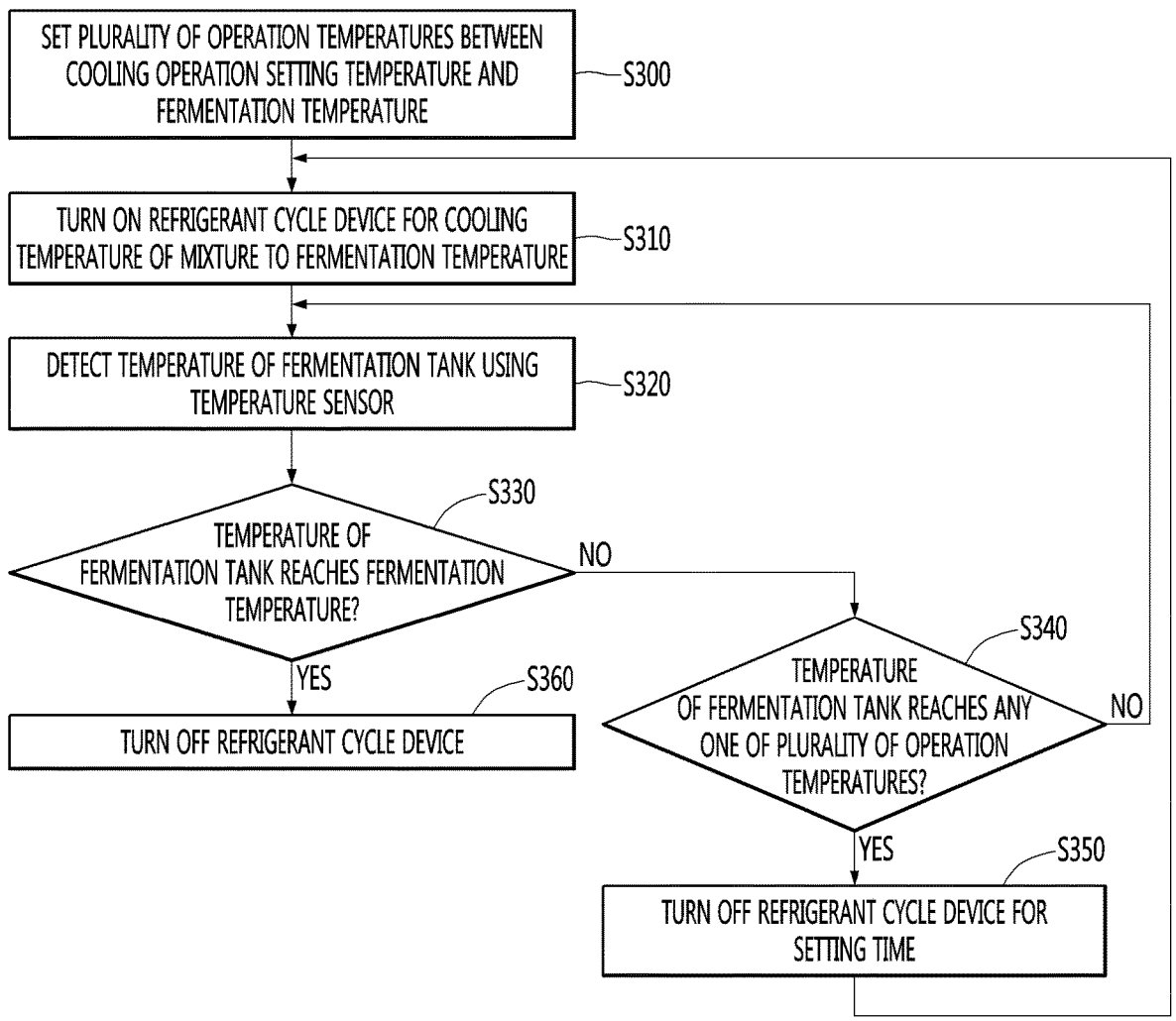
FIG. 6 is a flowchart of an operation for adjusting a temperature of a fermentation tank and a mixture accommodated therein to a fermentation temperature in order to perform a fermentation operation by a beverage maker according to an embodiment.

FIG. 6 is a flowchart of an operation for adjusting a temperature of a fermentation tank and a mixture accommodated therein to a fermentation temperature in order to perform a fermentation operation by a beverage maker according to an embodiment. Referring to FIG. 6, the beverage maker may set a plurality of step temperatures between the aforementioned cooling operation temperature (the third temperature TEMP3; see FIG. 5) and the fermentation temperature (S300).

The cooling operation temperature may be a fermentation tank temperature after the air supply and additives introduction operation (S120) are completed, and may correspond to the third temperature TEMP3 of FIG. 5. For example, the third temperature TEMP3 may be 30° C.; however, embodiments are not limited thereto.

For example, information on the plurality of step temperatures may be pre-stored in the memory 430, and the controller 440 may perform a setting operation using the information on the plurality of step temperatures stored in the memory 430. The fermentation temperature and the plurality of step temperatures may be different from each other depending on a type of the made beverage. In some embodiments, the controller 440 may also generate and set the plurality of step temperatures based on a current temperature of the fermentation tank 112 and the fermentation temperature depending on a type of the made beverage.

The beverage maker may drive the refrigerant cycle device 13 in order to cool a temperature of the fermentation tank 112 or a mixture accommodated in the fermentation container 12 to the fermentation temperature (S310). In general, the fermentation temperature may be higher than the cooling operation temperature, and thus, the controller 440 may drive the compressor 131 of the refrigerant cycle device 13 to initiate cooling of the fermentation tank 112.

As the compressor 131 is driven, a refrigerant may be supplied to the evaporator 134 wound around the external surface of the fermentation tank 112. A temperature of the evaporator 134 to which the refrigerant is supplied may be lowered, and the temperature of the fermentation tank 112 of an adjacent region to the evaporator 134 and a mixture therein may also be lowered. As the temperature of the fermentation tank 112 is lowered, the temperature of the mixture accommodated in the fermentation tank 112 may also be gradually lowered according to heat conduction and heat convection. The beverage maker may detect the temperature of the fermentation tank 112 using the temperature sensor 16 (S320).

As described above, the fermentation tank temperature of a portion adjacent to the evaporator 134 may have a high difference, for example, 20° C. or greater, with the temperature of the mixture in the fermentation tank 112, and thus, the temperature sensor 16 may be spaced apart from the evaporator 134 and may detect the temperature of the fermentation tank 112, and thus, may more accurately detect the temperature of the mixture. That is, the temperature of the fermentation tank 112 detected by the temperature sensor 16 may correspond to the temperature of the mixture. The beverage maker may drive the refrigerant cycle device 13 until the detected temperature reaches the fermentation temperature (S330).

Before the detected temperature reaches the fermentation temperature (NO in S330), the detected temperature may reach any one of the plurality of step temperatures (YES in S340). In this case, the beverage maker may stop driving the refrigerant cycle device 13 for a predetermined period of time (S350).

When the detected temperature reaches any one of the plurality of step temperatures, the controller 440 may stop driving the compressor 131 included in the refrigerant cycle device 13. As driving of the compressor 131 is stopped, refrigerant supply to the evaporator 134 may be stopped.

As refrigerant supply is stopped, the temperature of the fermentation tank 112 and the mixture therein of the evaporator 134 and an adjacent region to the evaporator 134 may be gradually increased. As the temperature of the mixture of the adjacent region to the evaporator 134 is increased, an activation degree of yeast present in the corresponding region may be increased, thereby increasing an entire activation degree of yeast in the mixture. In addition, as driving of the compressor 131 is stopped, a speed of lowering the temperature of the mixture may be reduced. As a result, reduction in the activation degree of yeast due to rapid temperature change of the mixture may be prevented.

In some embodiments, the beverage maker may also maintain the temperature of the fermentation tank 112 as the step temperature for the predetermined period of time. In this case, the controller 440 may also drive the refrigerant cycle device 13 or the heater 14 along with a temperature change of the fermentation tank 112.

After the predetermined period of time has elapsed, the beverage maker may re-drive the refrigerant cycle device 13 (S310). That is, as the refrigerant cycle device 13 is driven, the temperature detected by the temperature sensor 16 may reach the plurality of step temperatures in descending order and may lastly reach the fermentation temperature. Whenever the detected temperature reaches the plurality of step temperatures, the beverage maker may stop driving of the refrigerant cycle device 13 for the predetermined period of time, thereby achieving the aforementioned effect. When the detected temperature reaches the fermentation temperature (YES in S330), the beverage maker may stop driving the refrigerant cycle device 13 (S360) and may perform the fermentation operation.

Although not shown, the controller 440 may periodically detect the temperature of the fermentation tank 112 using the temperature sensor 16 during the fermentation operation. In this case, the temperature of the fermentation tank 112 may be changed depending on an external environment (external temperature). For example, when the detected temperature is higher than the fermentation temperature by a predetermined value or greater, the controller 440 may drive the refrigerant cycle device 13 to cool the temperature of the fermentation tank 112 to the fermentation temperature. In contrast, when the detected temperature is lower than the fermentation temperature by a predetermined value or greater, the controller 440 may increase the temperature of the fermentation tank 112 to the fermentation temperature.

Figure 7:
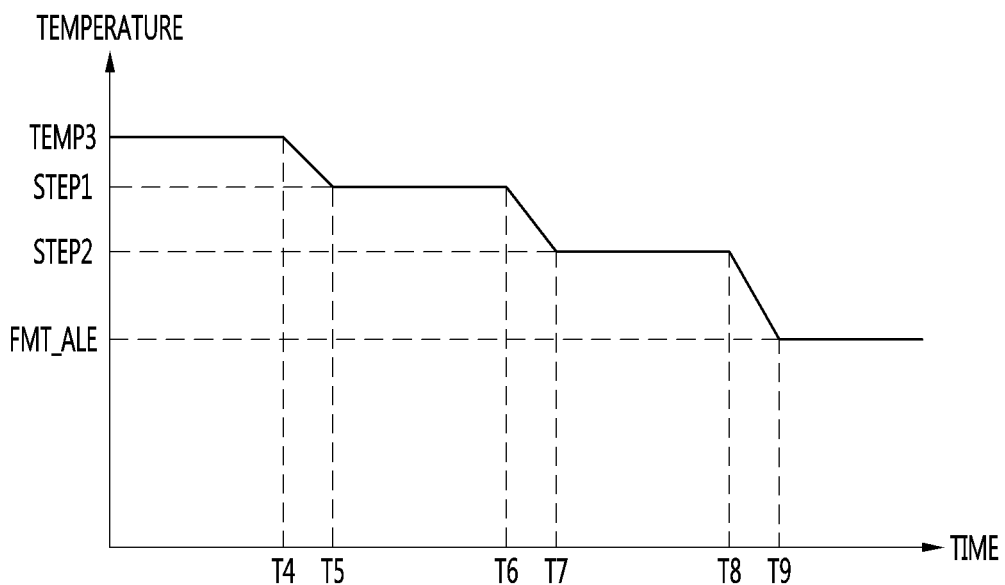
FIG. 7 is a graph showing an example of a temperature change detected by a temperature sensor when a beverage maker adjusts a fermentation temperature for making a first type of beverage with regard to the embodiment shown in FIG. 6.

FIG. 7 is a graph showing an example of a temperature change detected by a temperature sensor when a beverage maker adjusts a fermentation temperature for making a first type of beverage with regard to the embodiment shown in FIG. 6. In the embodiment of FIG. 7, the first type of beverage may be assumed to be an ale type beer. In this case, a fermentation temperature FMT_ALE may be about 21° C.

Referring to FIG. 7, the beverage maker may maintain the third temperature TEMP3 described above in FIG. 5 for a predetermined period of time, for example, about 3 hours to 6 hours. The third temperature TEMP3 may be about 28° C. to 35° C., that is, a temperature for maximizing an activation degree of yeast.

At a fourth time point T4 after the predetermined period of time has elapsed, the controller 440 may drive the refrigerant cycle device 13, more particularly, the compressor 131, and may cool the fermentation tank 112 and a mixture accommodated therein. The controller 440 may periodically detect the temperature of the fermentation tank 112 through the temperature sensor 16. As the refrigerant cycle device 13 is driven, the temperature detected by the temperature sensor 16 may be gradually lowered.

When the detected temperature reaches a first step temperature STEP1 among the plurality of step temperatures at a fifth time point T5, the controller 440 may stop driving the refrigerant cycle device 13 for a predetermined period of time. As driving of the refrigerant cycle device 13 is stopped, the temperature of the fermentation tank 112 of an adjacent region to the evaporator 134 and a mixture therein may be increased and may gradually reach the first step temperature STEP1 as the predetermined period of time elapses. In some embodiments, the controller 440 may also control the refrigerant cycle device 13 or the heater 14 to maintain the temperature detected by the temperature sensor 16 as the first step temperature STEP1 or a temperature within a predetermined range from the first step temperature STEP1 for the predetermined period of time.

At a sixth time point T6 after the predetermined period of time has elapsed, the controller 440 may re-drive the refrigerant cycle device 13 and may cool the fermentation tank 112 and a mixture accommodated therein. When the detected temperature reaches a second step temperature STEP2 that is lower than the first step temperature STEP1 at a seventh time point T7, the controller 440 may stop driving of the refrigerant cycle device 13 for the predetermined period of time. For example, the first step temperature STEP1 and the second step temperature STEP2 may be set with a constant temperature interval between the third temperature TEMP3 and the fermentation temperature FMT_ALE; however, embodiments are not limited thereto. When the first step temperature STEP1 and the second step temperature STEP2 are set with the constant temperature interval, the predetermined period of time for which driving of the refrigerant cycle device 13 is stopped may be constant. As driving of the refrigerant cycle device 13 is stopped, the temperature of the fermentation tank 112 of an adjacent region to the evaporator 134 and a mixture therein is increased and may gradually reach the second step temperature STEP2 as the predetermined period of time elapses.

At an eighth time point T8 after the predetermined period of time has elapsed, the controller 440 may re-drive the refrigerant cycle device 13 and may cool the fermentation tank 112 and a mixture accommodated therein. When the detected temperature reaches the fermentation temperature FMT_ALE at a ninth time point T9, the controller 440 may stop driving the refrigerant cycle device 13.

The controller 440 may control the refrigerant cycle device 13 or the heater 14 to maintain the temperature of the fermentation tank 112 and the mixture accommodated therein as the fermentation temperature FMT_ALE or a temperature within a predetermined range from the fermentation temperature FMT_ALE up to a time point of completing the fermentation operation.

Figure 8:
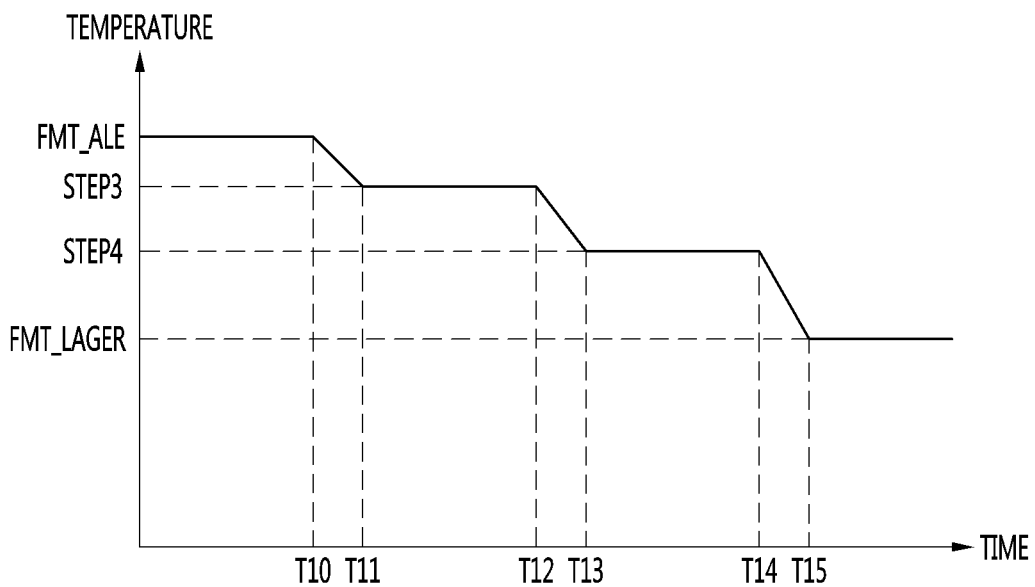
FIG. 8 is a graph showing an example of a temperature change detected by a temperature sensor when a beverage maker adjusts a fermentation temperature for making a second type of beverage with a lower fermentation temperature than the first type of beverage with regard to the embodiment shown in FIG. 6.

FIG. 8 is a graph showing an example of a temperature change detected by a temperature sensor when a beverage maker adjusts a fermentation temperature for making a second type of beverage with a lower fermentation temperature than the first type of beverage with regard to the embodiment shown in FIG. 6. In the embodiment of FIG. 8, the second type of beverage may be assumed to be a lager type beer.

The lager type beer may have a lower fermentation temperature than the ale type beer. For example, a fermentation temperature FMT_LAGER of the second type of beverage may be about 12° C. Accordingly, FIG. 8 illustrates the case in which the beverage maker cools the temperature of the fermentation tank 112 and the mixture to the fermentation temperature FMT_ALE of the first type of beverage according to the embodiment shown in FIG. 7 and then cools the fermentation tank 112 and the mixture based on the plurality of step temperatures STEP3 and STEP4 set between the fermentation temperature FMT_ALE of the first type of beverage and the fermentation temperature FMT_LAGER. However, in some embodiments, the beverage maker may also cool the fermentation tank 112 and the mixture based on the plurality of step temperatures set between the third temperature TEMP3 and the fermentation temperature FMT_LAGER.

Referring to FIG. 8, the beverage maker may cool the fermentation tank 112 and the mixture accommodated therein to the fermentation temperature FMT_ALE of the first type of beverage from the third temperature TEMP3 as described above in FIG. 7.

After the temperature of the fermentation tank 112 and the mixture accommodated therein is maintained at the fermentation temperature FMT_ALE for the predetermined period of time, the controller 440 may drive the refrigerant cycle device 13 at a tenth time point T10 and may cool the fermentation tank 112 and the mixture accommodated therein.

The controller 440 may periodically detect the temperature of the fermentation tank 112 through the temperature sensor 16. As the refrigerant cycle device 13 is driven, the temperature detected by the temperature sensor 16 may be gradually lowered.

When the detected temperature reaches a third step temperature STEP3 among the plurality of step temperatures STEP3 and STEP4 at an eleventh time point T11, the controller 440 may stop driving the refrigerant cycle device 13 for a predetermined period of time. As driving of the refrigerant cycle device 13 is stopped, the temperature of the fermentation tank 112 of an adjacent region to the evaporator 134 and a mixture therein may be increased, and may gradually reach the third step temperature STEP3 as the predetermined period of time elapses.

In some embodiments, the controller 440 may also control the refrigerant cycle device 13 or the heater 14 to maintain the temperature detected by the temperature sensor 16 as the third step temperature STEP3 or a temperature within a predetermined range from the third step temperature STEP3 for the predetermined period of time.

At a twelfth time point T12 after the predetermined period of time has elapsed, the controller 440 may re-drive the refrigerant cycle device 13 and may cool the fermentation tank 112 and the mixture accommodated therein. When the detected temperature reaches a fourth step temperature STEP4 that is lower than the third step temperature STEP3 at a thirteenth time point T13, the controller 440 may stop driving the refrigerant cycle device 13 for a predetermined period of time. For example, the third step temperature STEP3 and the fourth step temperature STEP4 may be set with a constant temperature interval between the fermentation temperature FMT_ALE of the first type of beverage and the fermentation temperature FMT_LAGER; however, embodiments are not limited thereto. When the third step temperature STEP3 and the fourth step temperature STEP4 are set with the constant temperature interval, the predetermined period of time for which driving of the refrigerant cycle device 13 is stopped may be constant. As driving of the refrigerant cycle device 13 is stopped, the temperature of the fermentation tank 112 of an adjacent region to the evaporator 134 and a mixture therein is increased and may gradually reach the fourth step temperature STEP4 as the predetermined period of time elapses.

At a fourteenth time point T14 after the predetermined period of time has elapsed, the controller 440 may re-drive the refrigerant cycle device 13 and may cool the fermentation tank 112 and a mixture accommodated therein. When the detected temperature reaches the fermentation temperature FMT_LAGER at a fifth time point T15, the controller 440 may stop driving the refrigerant cycle device 13.

The controller 440 may control the refrigerant cycle device 13 or the heater 14 to maintain the temperature of the fermentation tank 112 and the mixture accommodated therein as the fermentation temperature FMT_LAGER or a temperature within a predetermined range from the fermentation temperature FMT_LAGER up to a time point of completing the fermentation operation.

That is, according to embodiments shown in FIGS. 6 to 8, the beverage maker may control a thermostat to maintain each of the plurality of step temperatures for a predetermined period of time when temperatures of a mixture of a beverage ingredient and water in the fermentation tank are cooled, and thus, a rapid temperature change of the mixture may be prevented and reduction in an activation degree of yeast may be minimized.

In addition, the beverage maker may turn off driving of the refrigerant cycle device at the plurality of step temperatures for the predetermined period of time, and thus, refrigerant is continuously supplied to the evaporator, thereby overcoming a problem in terms of reduction in an activation degree of yeast present in an adjacent region of the fermentation tank around which the evaporator is wound. Accordingly, an activation degree of yeast may be increased, and thus, fermentation of the mixture may be more effectively performed, thereby enhancing quality or taste of the finished beverage.

Embodiments disclosed herein provide a beverage maker for minimizing an activation degree of yeast put into a fermentation tank when a temperature of a mixture of beverage ingredient and a fluid, such as water in a fermentation tank or a fermentation container is cooled.

A beverage maker according to embodiments may drive a refrigerant cycle device to cool a temperature of a fermentation tank in which a mixture including an ingredient of the beverage is accommodated in order to perform a fermentation operation during a beverage making procedure. In this case, when the temperature detected by a temperature sensor disposed in the fermentation tank reaches any one of a plurality of step temperatures set higher than the fermentation temperature, driving of the refrigerant cycle device may be stopped, and after a predetermined period of time has elapsed, the refrigerant cycle device may be re-driven. In this case, degradation of an activation degree of yeast due to continuous driving of a refrigerant cycle device may be prevented.

The refrigerant cycle device may include an evaporator wound around a portion of an external surface of the fermentation tank, and a temperature sensor may be spaced apart from the evaporator. Thus, when the refrigerant cycle device is driven, temperatures of a mixture and a fermentation tank of an adjacent region to the evaporator may be relatively lowered, and thus, an activation degree of yeast present in the corresponding region may be degraded. Thus, the beverage maker may stop driving the refrigerant cycle device at the step temperature, and thus, the activation degree of yeast of the region may be minimized.

The plurality of step temperatures may be set at a constant temperature interval between the fermentation temperature and the fermentation tank temperature prior to driving of the refrigerant cycle device. The beverage maker may control the refrigerant cycle device or a heater to maintain the temperature detected by the temperature sensor as the reached step temperature or a temperature within a predetermined range from the reached step temperature for the predetermined period of time.

When the temperature detected by the temperature sensor reaches the fermentation temperature, the beverage maker may stop driving the refrigerant cycle device and may control the refrigerant cycle device or the heater to maintain the temperature detected by the temperature sensor as the fermentation temperature or a temperature within a predetermined range from the fermentation temperature. The controller of the beverage maker may directly generate and set the plurality of step temperatures based on the fermentation temperature and the fermentation tank temperature prior to driving of the refrigerant cycle device.

Details of one or more embodiments are set forth in the accompanying drawings and the description. Other features will be apparent from the description and drawings, and from the claims. The disclosed subject matter is to be considered illustrative, and not restrictive, and the appended claims are intended to cover all such modifications, enhancements, and other implementations, which fall within the scope. Thus, implementation of embodiments is to be considered illustrative, and not restrictive. Therefore, the scope is defined not by the detailed description but by the appended claims, and all differences within the scope will be construed as being included.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A beverage maker, comprising:
   a fermentation tank including a space in which a beverage is made;
   a refrigerant cycle device configured to cool the fermentation tank, the refrigerant cycle device comprising:
      an evaporator wound around a portion of an external surface of the fermentation tank, wherein the evaporator is disposed to contact an outer surface of the fermentation tank; and
      a compressor configured to supply a refrigerant to the evaporator;
   a heater disposed below the fermentation tank, the heater installed to contact a bottom surface of the fermentation tank;
   a temperature sensor configured to detect a temperature of the fermentation tank, the temperature sensor disposed on the external surface of the fermentation tank and spaced apart from the evaporator; and
   a controller configured to drive the compressor to decrease the temperature in the fermentation tank which accommodates a mixture including water and wort to a fermentation temperature while the beverage is being made, to supply yeast into the fermentation tank in response to determining that the temperature detected by the temperature sensor reaches a reference temperature, to stop driving of the compressor in response to determining that the temperature detected by the temperature sensor reaches a first step temperature of a plurality of step temperatures, which is higher than the fermentation temperature, and to re-drive the compressor after a predetermined period of time has elapsed, wherein the reference temperature is higher than the first step temperature, wherein the controller drives the compressor in response to determining that the temperature detected by the temperature sensor is higher than the first step temperature by a reference value or greater for the predetermined period of time.

2. The beverage maker of claim 1, wherein the plurality of step temperatures has a constant temperature interval between the fermentation temperature and a temperature of the fermentation tank prior to the driving of the compressor.

3. The beverage maker of claim 1, wherein the controller controls the compressor or the heater to maintain the temperature detected by the temperature sensor as the first step temperature or a temperature within a predetermined range from the first step temperature for the predetermined time.

4. The beverage maker of claim 3, wherein the controller drives the heater in response to a determination that the temperature detected by the temperature sensor is lower than the first step temperature by a predetermined value or greater for the predetermined period of time.

5. The beverage maker of claim 3, wherein the controller stops the driving of the compressor in response to determining that the detected temperature reaches the fermentation temperature, and controls the compressor or the heater to maintain the temperature detected by the temperature sensor as the fermentation temperature or a temperature within a predetermined range from the fermentation temperature up to a time point of completing fermentation.

6. The beverage maker of claim 1, wherein the plurality of step temperatures is based on the fermentation temperature and a temperature of the fermentation tank prior to the driving of the compressor.

7. The beverage maker of claim 6, wherein the plurality of step temperatures is between the fermentation tank temperature and the fermentation temperature.

8. A beverage maker, comprising:
   a fermentation tank including a space in which a beverage is made;
   a refrigerant cycle device configured to cool the fermentation tank, the refrigerant cycle device comprising:
      an evaporator wound around a portion of an external surface of the fermentation tank, wherein the evaporator is disposed to contact an outer surface of the fermentation tank; and
      a compressor configured to supply a refrigerant to the evaporator;
   a heater disposed below the fermentation tank, the heater installed to contact a bottom surface of the fermentation tank;
   a temperature sensor configured to detect a temperature of the fermentation tank, the temperature sensor disposed on the external surface of the fermentation tank and spaced apart from the evaporator; and
   a controller configured to drive the compressor to decrease the temperature in the fermentation tank which accommodates a mixture including water and wort to a fermentation temperature while the beverage is being made, to supply yeast into the fermentation tank in response to determining that the temperature detected by the temperature sensor reaches a reference temperature, to stop driving of the compressor in response to determining that the temperature detected by the temperature sensor reaches a first step temperature of a plurality of step temperatures, is higher than the fermentation temperature, and to re-drive the compressor after a predetermined period of time has elapsed, and repeating the stopping the driving and the redriving the compressor for each of the plurality of step temperatures until the fermentation temperature is reached, wherein the reference temperature is higher than the first step temperature, wherein the controller drives the compressor in response to determining that the temperature detected by the temperature sensor is higher than the first step temperature by a reference value or greater for the predetermined period of time.

9. The beverage maker of claim 8, wherein the plurality of step temperatures has a constant temperature interval between the fermentation temperature and a temperature of the fermentation tank prior to the driving of the compressor.

10. The beverage maker of claim 8, wherein the plurality of step temperatures is based on the fermentation temperature and a temperature of the fermentation tank prior to the driving of the compressor.

11. The beverage maker of claim 10, wherein the plurality of step temperatures is between the fermentation tank temperature and the fermentation temperature.

* * * * *